(12) United States Patent
Hee-Hanson et al.

(10) Patent No.: US 12,268,858 B1
(45) Date of Patent: Apr. 8, 2025

(54) INJECTOR DEVICE

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/594,683

(22) Filed: Mar. 4, 2024

(51) Int. Cl.
*A61M 5/32* (2006.01)

(52) U.S. Cl.
CPC ........ *A61M 5/3243* (2013.01); *A61M 5/3202* (2013.01); *A61M 2205/0216* (2013.01)

(58) Field of Classification Search
CPC ........ A61M 2205/0216; A61M 5/3202; A61M 5/3205; A61M 5/321; A61M 5/3243; A61M 5/3245; A61M 5/3271; A61M 5/3275; A61M 5/24; A61M 5/32; A61M 2005/2403; A61M 2005/2407; A61M 2005/2485; A61M 2005/2492
See application file for complete search history.

(56) References Cited

U.S. PATENT DOCUMENTS

| | | | |
|---|---|---|---|
| 5,356,387 A | 10/1994 | Sirbola | |
| 7,597,685 B2 | 10/2009 | Olson | |
| 8,048,035 B2 | 11/2011 | Mesa et al. | |
| 8,945,063 B2 * | 2/2015 | Wotton | A61P 19/02 604/218 |

(Continued)

FOREIGN PATENT DOCUMENTS

| | | |
|---|---|---|
| CH | 705345 A2 | 2/2013 |
| CH | 705992 A2 | 6/2013 |

(Continued)

OTHER PUBLICATIONS

Needle-based injection systems for medical use Requirements and test methods, Part 1: Needle injection systems, ISO 11608 1:2014(E), Third Edition, Switzerland, ISO, Dec. 15, 2014, pp. 1-13.

(Continued)

*Primary Examiner* — Shefali D Patel
(74) *Attorney, Agent, or Firm* — Fish & Richardson P.C.

(57) ABSTRACT

A medicament delivery device reduces a force required for activation, and the medicament delivery device comprises: a needle at a distal end of the device; a needle cover and a body, wherein the needle cover is axially movable relative to the body between an initial position, in which the needle cover covers the needle, and an activated position for dispensing a medicament from the device; and a carrier configured to support a pre-filled syringe, wherein the carrier is disposed within the needle cover and comprises one or more resilient members, wherein the needle cover comprises one or more first slots and one or more second slots and the one or more resilient members are each configured to engage with a respective one of the one or more first slots when the needle cover is in the initial position, and to enter a respective one of the one or more second slots after a proximal movement of the needle cover from the initial position to an intermediate position.

30 Claims, 11 Drawing Sheets

(56) References Cited

U.S. PATENT DOCUMENTS

| | | |
|---|---|---|
| 9,216,256 B2 | 12/2015 | Olson et al. |
| 9,687,607 B2 * | 6/2017 | Brereton ............... A61M 5/326 |
| 10,569,019 B2 | 2/2020 | Hirschel et al. |
| 10,799,647 B2 | 10/2020 | Hostettler et al. |
| 11,116,911 B2 | 9/2021 | Wu |
| 11,383,044 B2 | 7/2022 | Tschirren et al. |
| 2004/0039336 A1 | 2/2004 | Amark et al. |
| 2005/0101919 A1 | 5/2005 | Brunnberg |
| 2007/0060840 A1 | 3/2007 | Conway |
| 2007/0112310 A1 | 5/2007 | Lavi et al. |
| 2007/0239117 A1 | 10/2007 | Chelak et al. |
| 2013/0289525 A1 | 10/2013 | Kemp et al. |
| 2017/0106146 A1 | 4/2017 | Folk et al. |
| 2019/0358400 A1 | 11/2019 | Nakamura et al. |
| 2020/0046909 A1 | 2/2020 | Hommann et al. |
| 2020/0289754 A1 | 9/2020 | Liscio et al. |
| 2021/0361881 A1 | 11/2021 | Garson et al. |
| 2021/0393886 A1 | 12/2021 | Nicolas et al. |

FOREIGN PATENT DOCUMENTS

| | | |
|---|---|---|
| EP | 3381490 B1 | 9/2020 |
| WO | WO 2002/047746 A1 | 6/2002 |
| WO | WO 2010/136077 A1 | 12/2010 |
| WO | WO 2018/011417 A1 | 1/2018 |
| WO | WO 2021/160540 A1 | 8/2021 |
| WO | WO 2021/197804 A1 | 10/2021 |
| WO | WO 2022/069617 A1 | 4/2022 |
| WO | WO 2022/184388 A1 | 9/2022 |
| WO | WO 2022/223789 A1 | 10/2022 |
| WO | WO 2023/057578 A1 | 4/2023 |

OTHER PUBLICATIONS

U.S. Appl. No. 18/594,556, filed Mar. 4, 2024, Alexander Hee-Hanson.

U.S. Appl. No. 18/594,643, filed Mar. 4, 2024, Alexander Hee-Hanson.

U.S. Appl. No. 18/594,597, filed Mar. 4, 2024, Alexander Hee-Hanson.

* cited by examiner

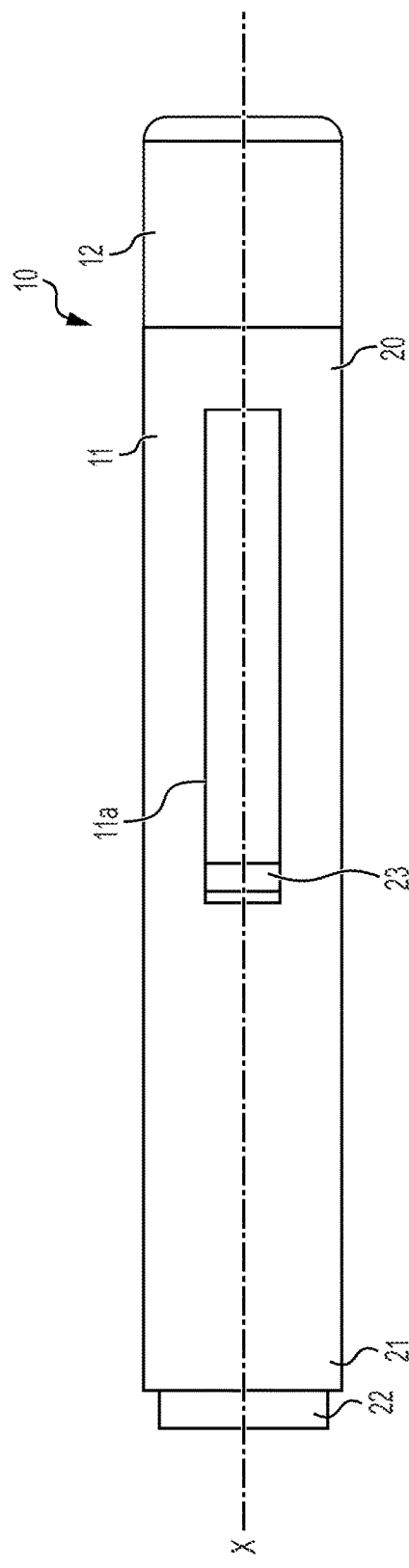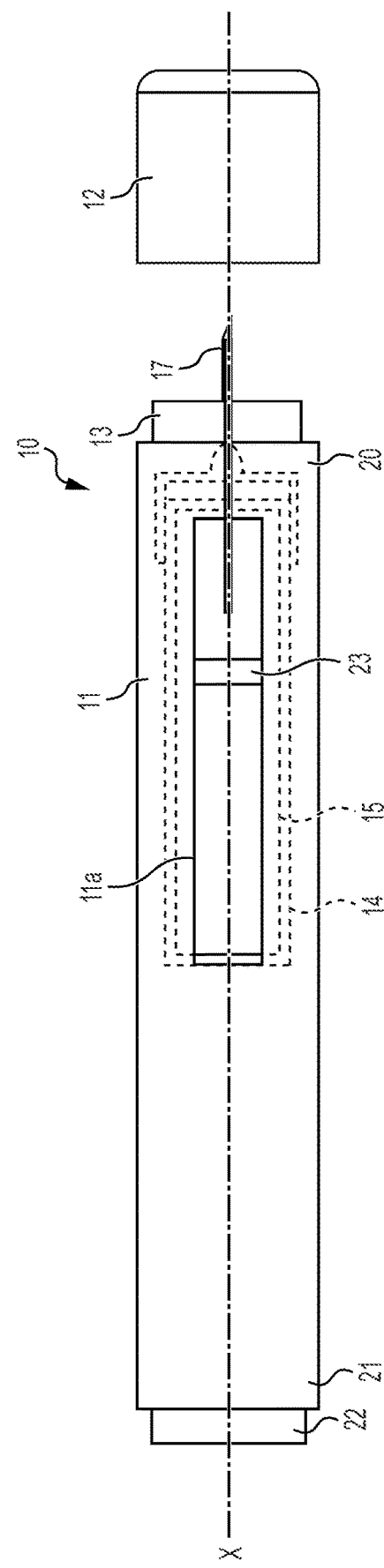
FIG. 1A
FIG. 1B

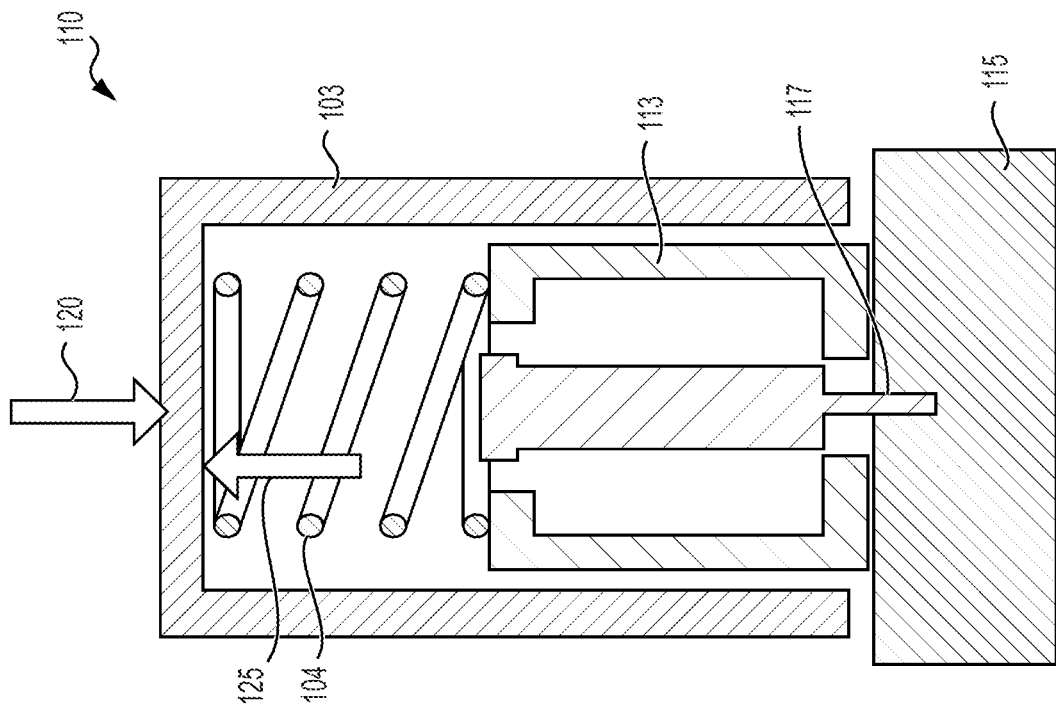
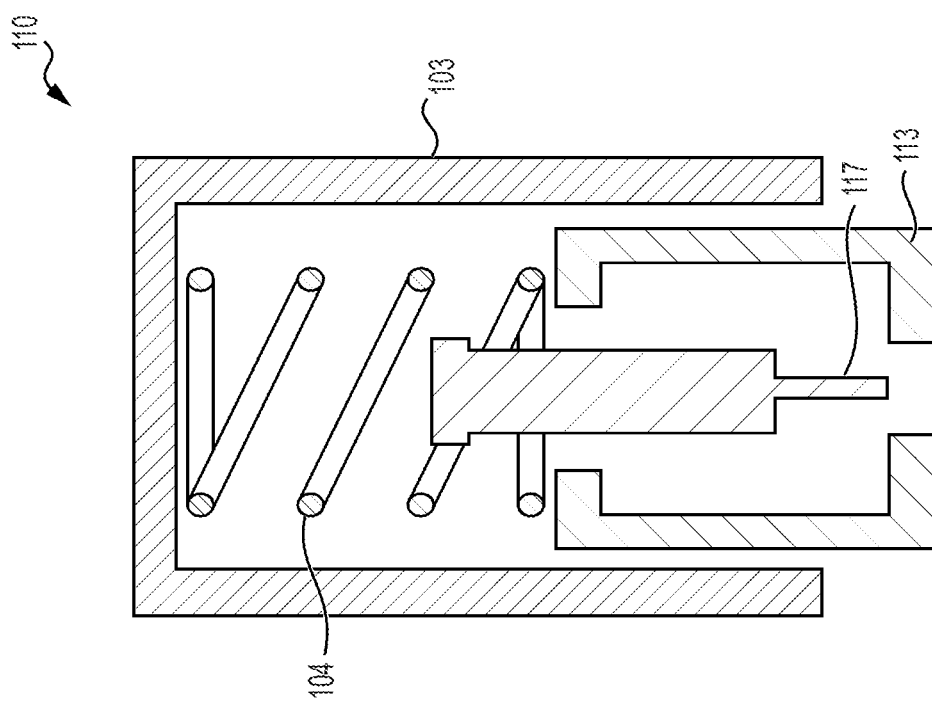

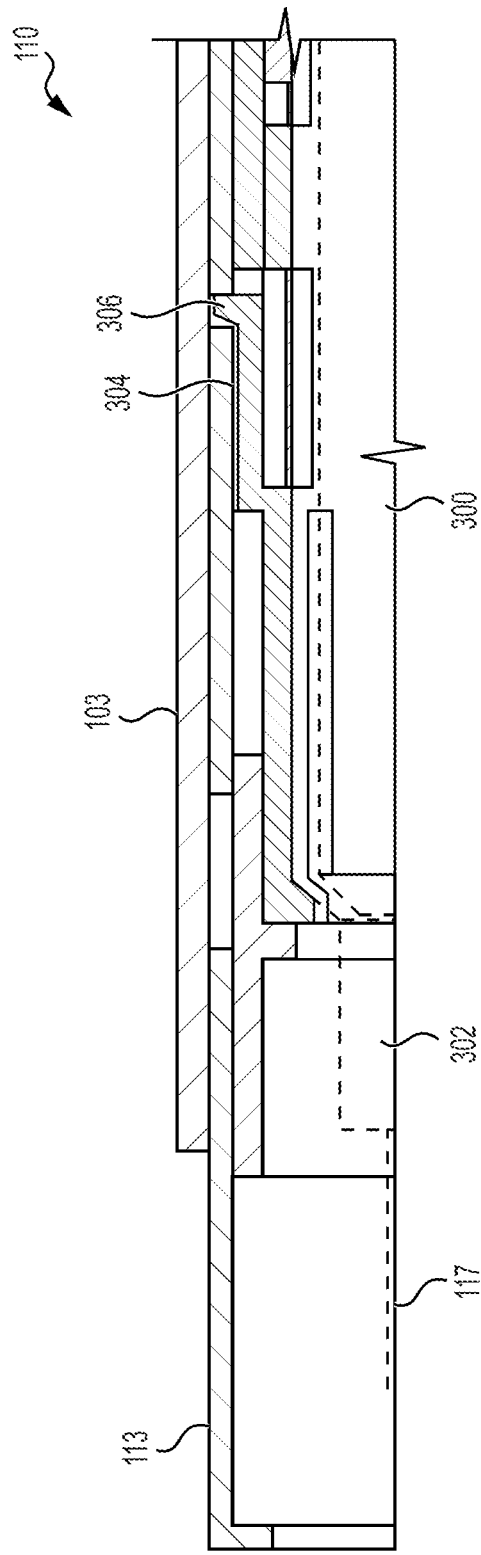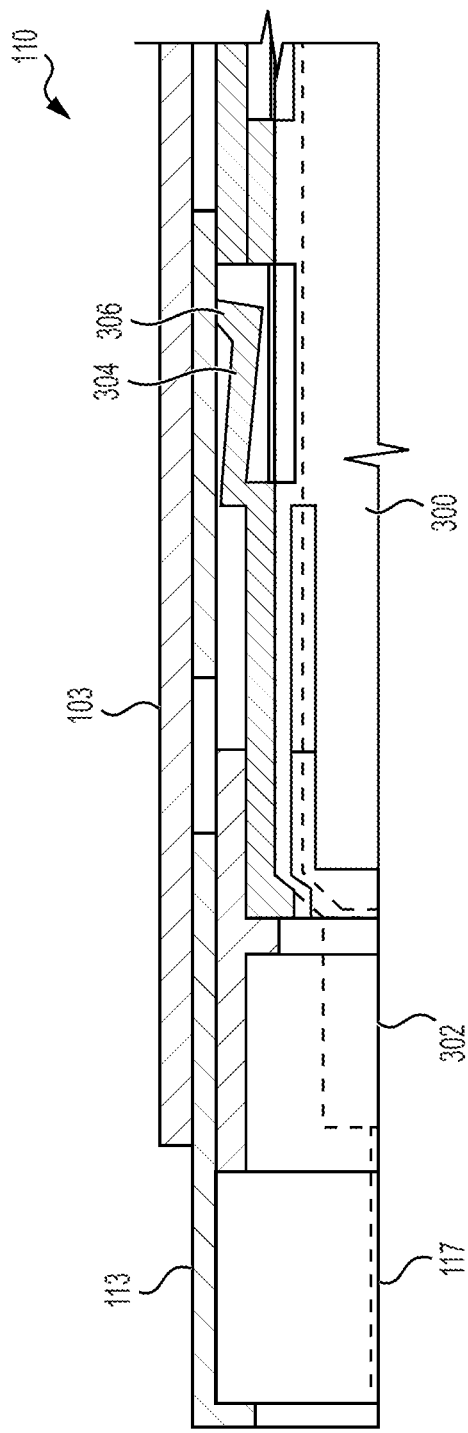
FIG. 3A
FIG. 3B

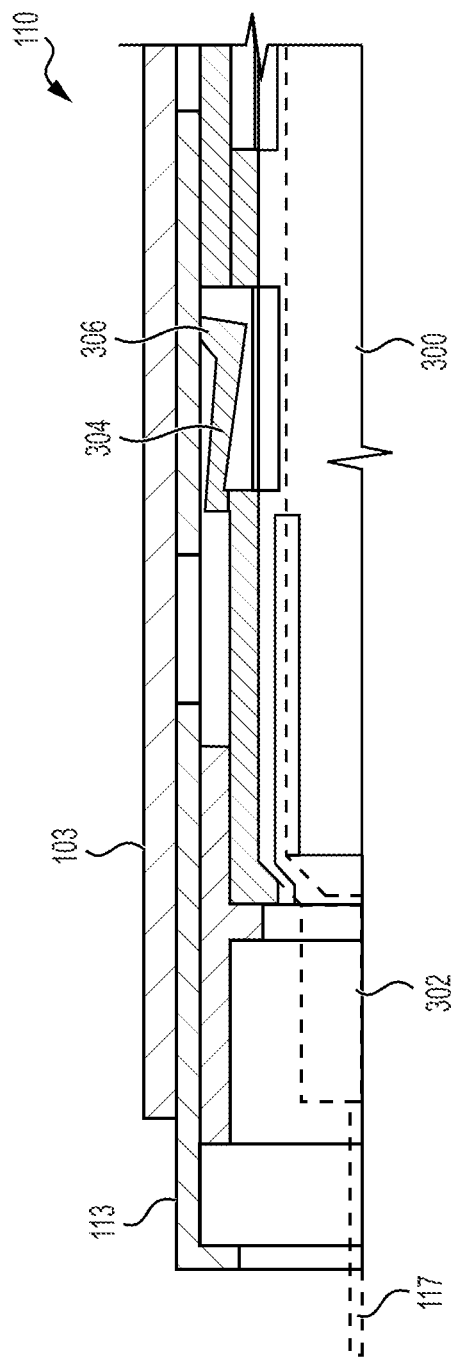
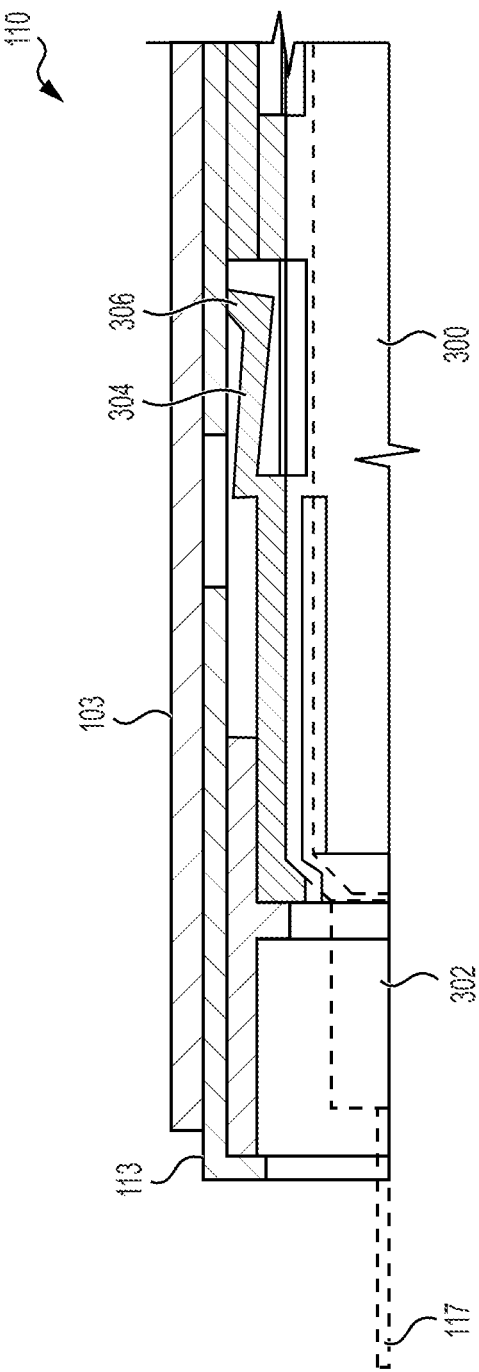

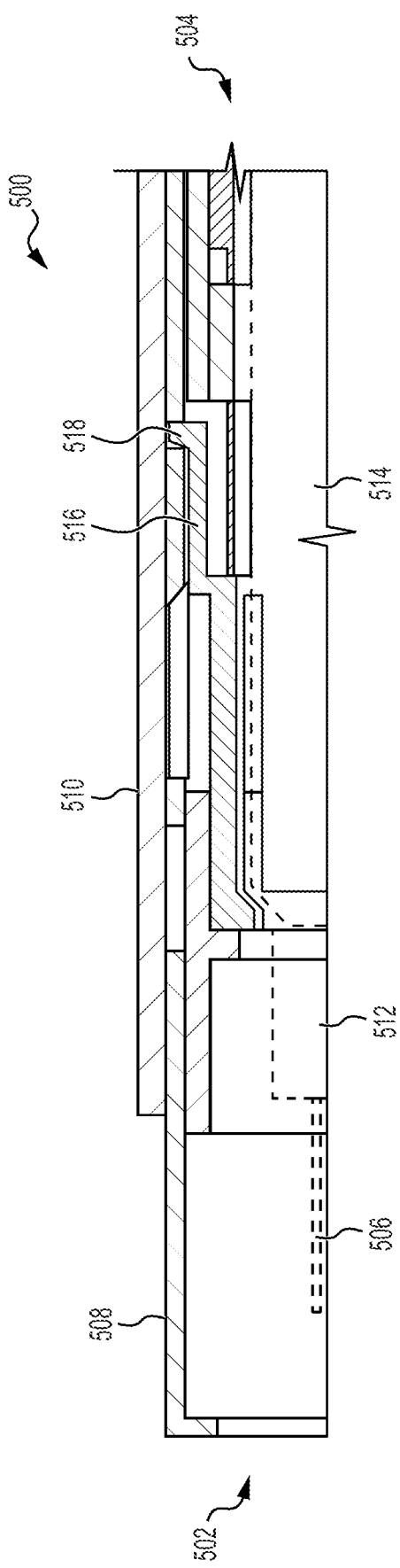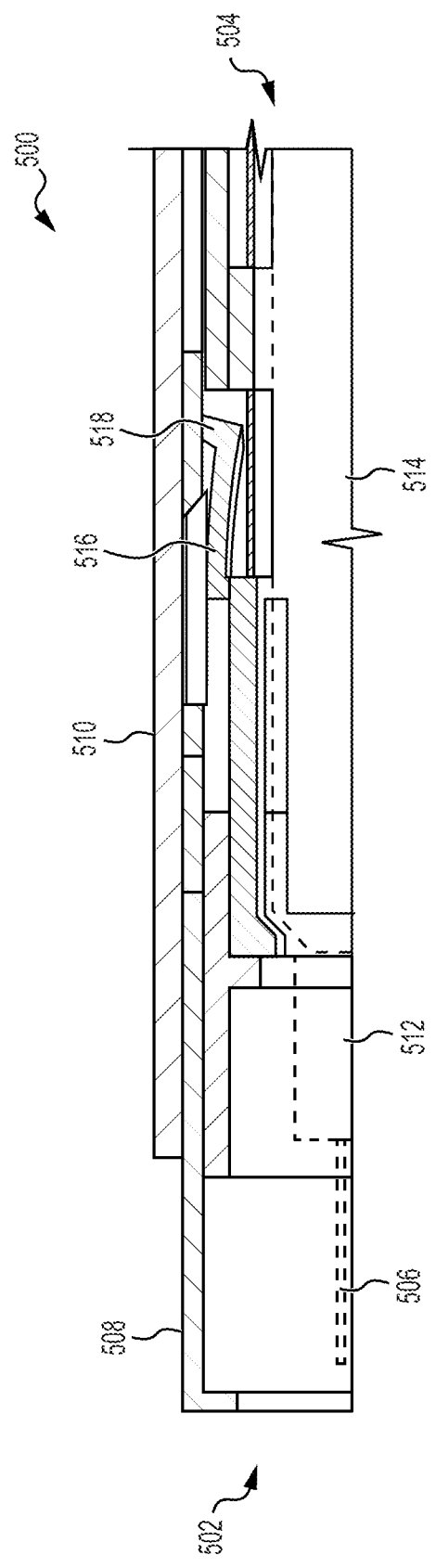

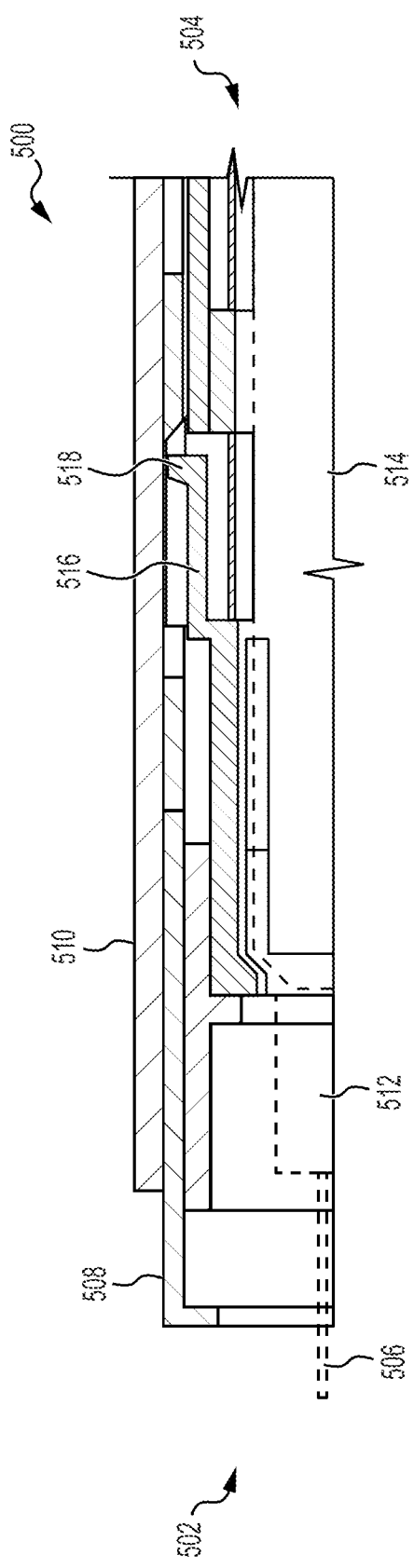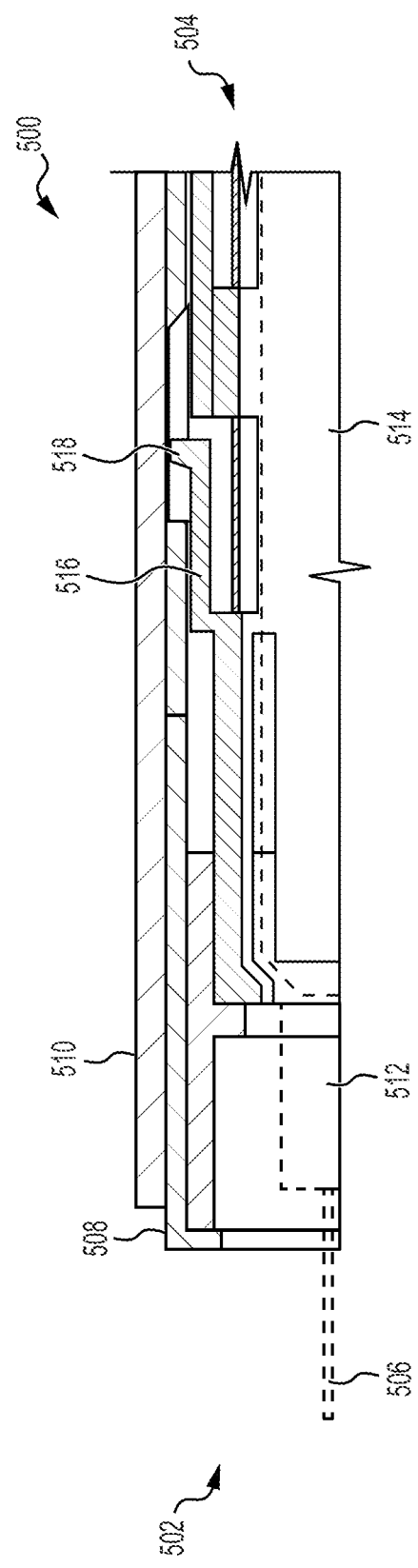

INJECTOR DEVICE

TECHNICAL FIELD

This application relates to an injector device for delivery of a medicament, particularly to an auto-injector device.

BACKGROUND

Injector devices are used to deliver a range of medicaments. In an auto-injector device, some or all of the actions required to use the injector device in administering medicament to a user are automated.

It is known to provide an auto-injector device having a needle cover which is axially movable to cover and uncover a needle, with the needle cover being biased by a spring to extend over the needle. Typically, the user presses the needle cover against an injection site, against the force of the spring, to push the needle cover into the housing and to uncover the needle which is pushed into the injection site. Medicament is automatically dispensed from the needle via an automated mechanism. A user typically holds the needle cover in a holding position for a predetermined period of time, to ensure that the correct dose of medicament is dispensed from the device, before removing the device from the injection site.

Some users find it difficult to fully depress the needle cover due to the force required or the change in force experienced during the activation movement. This may result in the needle not entering the user's skin to the correct depth, pain, discomfort, a wet injection site, early device removal and/or partial delivery of the medicament.

SUMMARY

A first aspect of this disclosure provides a medicament delivery device for reducing a force required to activate the medicament delivery device, wherein the medicament delivery device comprises:
  a needle for injecting medicament into a user, the needle disposed at a distal end of the medicament delivery device;
  a needle cover and a body, wherein the needle cover is axially movable relative to the body between an initial position, in which the needle cover covers the needle, and an activated position for dispensing medicament from the medicament delivery device, wherein in the activated position the needle protrudes from the distal end of the needle cover; and
  a carrier configured to support a pre-filled syringe, wherein the carrier is disposed within the needle cover and comprises one or more resilient members,
  wherein the needle covers comprises one or more first slots and the one or more resilient members are each configured to engage with a respective one of the one or more first slots when the needle cover is in the initial position,
  wherein the needle covers comprises one or more second slots and the one or more resilient members are each configured to enter a respective one of the one or more second slots after a proximal movement of the needle cover from the initial position to an intermediate position.

Between the initial position and the intermediate position, the one or more resilient members may each be configured to be deflected so as to contact an inner surface of the needle cover.

Movement of the needle cover proximally from the initial position may cause the one or more resilient members to disengage from the one or more first slots.

The one or more resilient members may each be configured to remain in the one or more second slots during proximal movement of the needle cover between the intermediate position and the activated position.

There may be a zero normal force between the one or more resilient members and the needle cover when the one or more resilient members are located in the second slots.

The one or more resilient members may each comprise a flexible arm and a protrusion disposed on an end of the flexible arm. The protrusion may be configured to:
  engage with a respective one of the one or more first slots when the needle cover is in the initial position;
  enter a respective one of the one or more second slots after a proximal movement of the needle cover from the initial position to an intermediate position; and
  contact an inner surface of the needle cover between the initial position and the intermediate position.

A distal facing edge of the protrusion may be beveled. Alternatively, or in addition, a proximal or outward facing edge of the protrusion may be beveled.

The one or more first slots and/or the one or more second slots may be apertures extending through the body of the needle cover.

The one or more first slots and/or the one or more second slots may be recesses in an inner surface of the needle cover.

The medicament delivery device may further comprise a spring configured to exert a spring force which biases the needle cover axially, towards the distal end of the medicament delivery device.

A distal facing edge of each of the one or more second slots may be beveled.

The needle may be configured to begin protruding from the distal end of the needle cover during movement between the intermediate and activated positions.

The medicament delivery device may further comprise the pre-filled syringe.

A second aspect of this disclosure provides a medicament delivery device for reducing a force required to activate the medicament delivery device, wherein the medicament delivery device comprises:
  a needle for injecting medicament into a user, the needle disposed at a distal end of the medicament delivery device;
  a needle cover and a body, wherein the needle cover is configured to be moved in a proximal direction into the body of the medicament delivery device to expose the needle;
  a pre-filled syringe carrier, wherein the pre-filled syringe carrier is disposed within the needle cover and comprises one or more flexible arms,
  wherein the one or more flexible arms are each configured:
  prior to activation of the medicament delivery device, to be retained in a respective first slot, aperture or recess in the needle cover;
  during an initial portion of an activation movement of the needle cover, to be forced out of the respective first slot, aperture or recess in the needle cover;
  during a subsequent portion of the activation movement of the needle cover, to move out of engagement with the needle cover so as to reduce a force required to move the needle cover in a proximal direction into the body of the medicament delivery device.

The needle cover may be configured to be moved in a proximal direction into the body of the medicament delivery device when a force is applied in a proximal direction to a distal end surface of the needle cover.

During the initial portion of the activation movement of the needle cover, the one or more flexible arms may each be configured to be deflected by contact with a surface of the needle cover. During the initial portion of the activation movement of the needle cover, the one or more flexible arms may each be biased against the surface of the needle cover.

During the initial portion of an activation movement of the needle cover, the one or more flexible arms may exert a frictional force against the surface of the needle cover which increases the force required to move the needle cover in a proximal direction into the body of the medicament delivery device.

The surface of the needle cover may be an inner circumferential surface.

During the subsequent portion of the activation movement of the needle cover, the one or more flexible arms may each be configured to move out of engagement with the needle cover by entering a respective second slot, aperture or recess in the needle cover.

The one or more flexible arms may exert zero normal force against the needle cover when out of engagement with the needle cover. The one or more flexible arms may exert zero frictional force against proximal movement of the needle cover when out of engagement with the needle cover.

The one or more flexible arms may each be configured to remain out of engagement with the needle cover for the remainder of the activation movement of the needle cover. A distal facing edge of the second slot, aperture or recess may be beveled.

Each of the one or more flexible arms may comprise a protrusion disposed on a free end of the flexible arm. The protrusion may be configured to: be retained in the respective first slot, aperture or recess in the needle cover when the needle cover is in an initial position, prior to activation of the medicament delivery device; contact an inner surface of the needle cover during proximal movement of the needle cover between the initial position and an intermediate position; and enter a respective second slot, aperture or recess in the needle cover when the needle cover reaches the intermediate position.

A distal facing edge of the protrusion may beveled. A proximal or outward facing edge of the protrusion may be beveled.

The medicament delivery device may further comprise a spring configured to exert a spring force which biases the needle cover axially, towards the distal end of the medicament delivery device.

BRIEF DESCRIPTION OF THE DRAWINGS

Reference is made to the accompanying drawings in which:

FIG. 1A shows an injector device with a cap attached;

FIG. 1B shows the injector device of FIG. 1A with the cap removed;

FIG. 2A shows a simplified view of an injector device prior to use;

FIG. 2B shows a view of the device of FIG. 2A with the injector device in the holding position;

FIG. 3A shows a device in a pre-use state;

FIG. 3B shows the device at the start of an activation movement;

FIG. 3C shows the device in a mid-activation state;

FIG. 3D shows the device in an activated state;

FIG. 5A shows a medicament delivery device in an initial state;

FIG. 5B shows the medicament delivery device at the start of an activation movement;

FIG. 5C shows the medicament delivery device in an intermediate position;

FIG. 5D shows the medicament delivery device in an activated state;

DETAILED DESCRIPTION

Figure 4A:
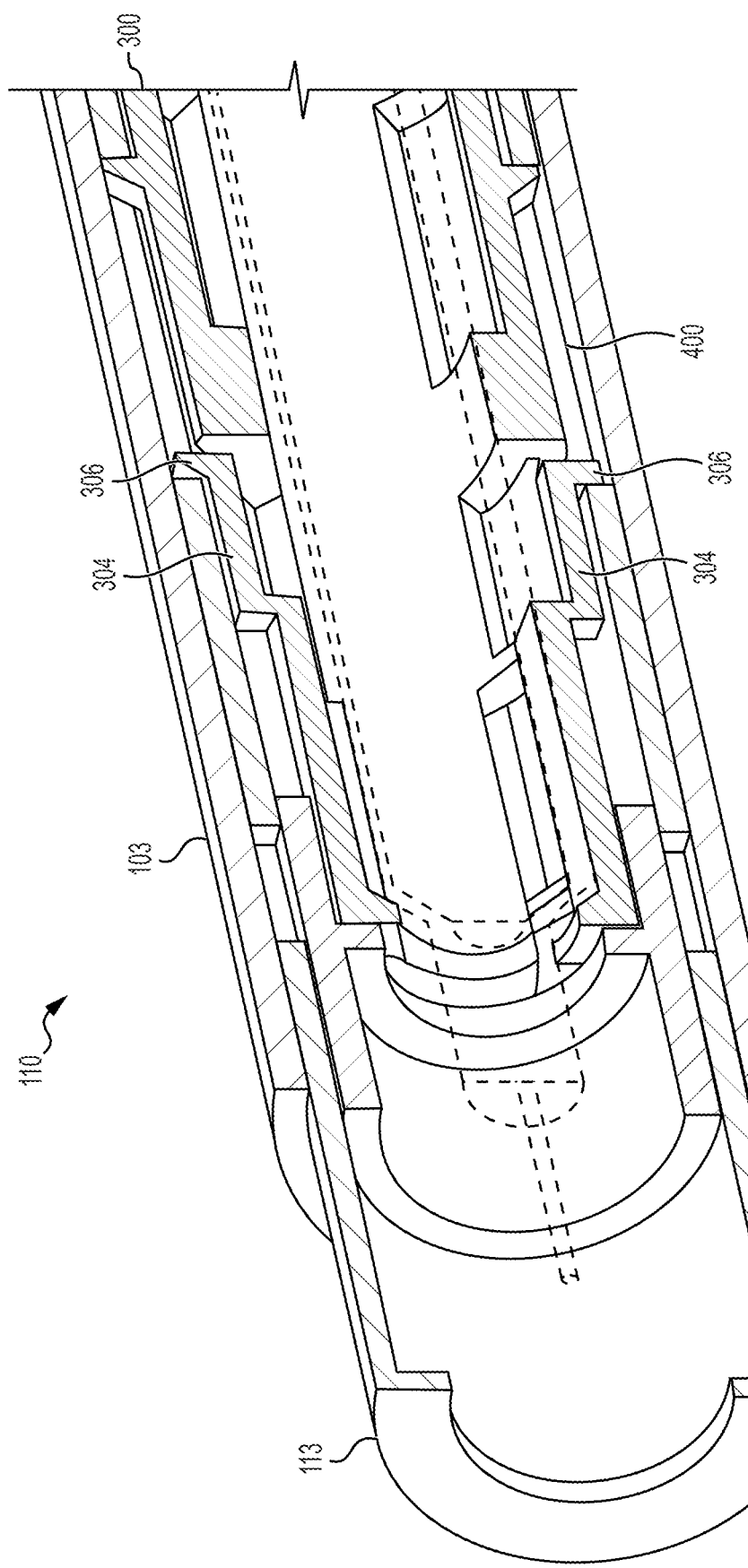
FIG. 4A is a perspective view of a cross section of the device in the initial state of FIG. 3A.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user removes cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIGS. 2A and 2B show a simplified view of a device 110 having a needle cover 113 which is axially movable to cover and uncover the needle 117. The needle cover 113 is biased by a spring 104 to extend over the needle 117.

FIG. 2A shows the device before use, in which the needle cover 113 is exposed out of the end of the device body 103 and covers the needle 117. A force can be applied by a user against a spring force 125 to move the needle cover 113 from the position shown in FIG. 2A towards a holding position shown in FIG. 2B, and a holding force 120 can be applied to maintain the needle cover in the holding position.

Typically the user presses the needle cover 113 against an injection site 115 to push the needle cover 113 at least partially into the device body 103. The exposed needle 117 is pushed into the injection site 115. In the holding position, medicament is automatically dispensed from the needle 117 via an automated mechanism. A user typically holds the needle cover 113 in the holding position for a predetermined period of time, to ensure that the correct dose of medicament is dispensed from the device 110, before removing the device from the injection site 115.

The spring force 125 against which the user applies a force to move the needle cover 113 is one component of the "activation force" of the device 110. The activation force refers to the force or force profile that the user exerts on the device 110 to move the needle cover 113 from the position shown in FIG. 2A to the position shown in FIG. 2B. If this force or force profile is not well balanced, it can lead to difficulty in activating the device 100 for some users, or increase the pain or anxiety associated with using the device.

FIGS. 3A to 3D show further details of the operation of the device 110. These Figures each show a cross section of the one half of the device 110 during various stages of activation of the device.

FIG. 3A shows the device in a pre-use state, may also be called an initial state or initial position. The needle cover 113 covers the needle 117 in this position. A spring may bias the needle cover 113 distally so that it extends over the needle 117. The device 110 also comprises a carrier 300, which supports a pre-filled syringe 302. The needle 117 is in fluid communication with the pre-filled syringe 302 and extends from the distal end of the pre-filled syringe 302. The carrier 300 comprises a resilient member 304 which takes the form of a flexible arm which extends axially (or longitudinally) and which has a protrusion 306 on the free end of the flexible arm. The protrusion 306 extends radially from the flexible arm to engage with a first slot in the needle cover 113.

Although one resilient member 304 is shown in FIG. 3A, the carrier 300 may comprise two or more resilient members 304. For example, two resilient members 304 may be disposed opposite each other on the carrier 300 and may engage with corresponding slots in the needle cover 113. Having the resilient member 304 engage a slot in the needle cover 113 in this initial position may prevent axial travel of the needle cover 113 during assembly of the device 110 and may help to prevent inadvertent activation of the device 110.

FIG. 3B shows the device 110 at the start of an activation movement. A distal force is applied via the body 103 while the needle cover 113 is placed against the user's skin, causing the needle cover 113 to move proximally into the device 110. During this initial movement, the resilient member 304 is deflected and exits the first slot in the needle cover 113. The resilient member 304 abuts an inner surface of the needle cover 113 resulting in a normal force between these components. This leads to a frictional force which resists proximal movement of the needle cover 113 into the device 110 and therefore increases the force required to activate the device 110.

FIG. 3C shows the device 110 in a mid-activation state. In this position, the needle 117 has protruded from the end of the needle cover 113, but the medicament dispensing mechanism of the device 110 has not yet been triggered. As can be seen, the resilient member 304 is still in a deflected state and still exerts and normal and frictional force on the needle cover 113.

FIG. 3D shows the device 110 in an activated state. In this position the needle cover 113 is fully displaced into the device 110, the needle 117 protrudes from the end of the needle cover 113 to its maximum extend and the medicament dispensing mechanism of the device 110 is triggered. As can be seen, the resilient member 304 is still in a deflected state and still exerts and normal and frictional force on the needle cover 113.

After the medicament has been delivered, during removal of the device 110, the sequence of FIGS. 3A to 3D is reversed. The resilient member 304 remains in a deflected state until the needle cover 113 returns to the initial position.

FIG. 4A is a perspective view of a cross section of the device 110 in the initial state (as also shown in FIG. 3A). In this view it can be seen that the protrusion 306 of the resilient member 304 abuts an end face of the slot 400 in the needle cover 113. The carrier 300 comprises two resilient members 304 on opposite sides and there are two corresponding slots 400 in the needle cover 113.

Figure 4B:
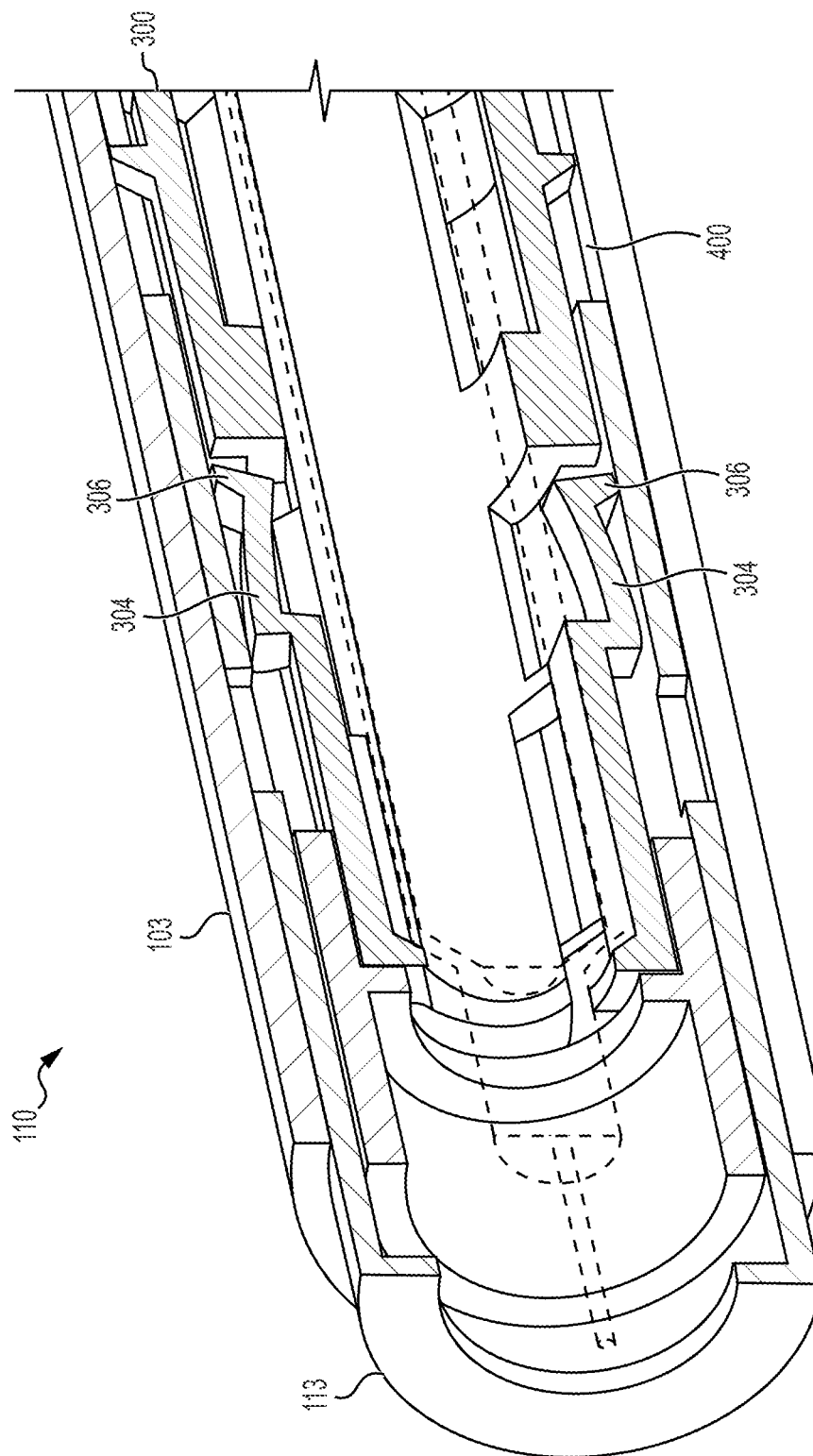
FIG. 4B is a perspective view of a cross section of the device in the mid-activation state of FIG. 3C.

FIG. 4B is a perspective view of a cross section of the device 110 in a mid-activation state (as also shown in FIG. 3C). In this view it can be seen that the resilient members 304 are deflected, so that the protrusions 306 on the free ends of the flexible arms contact the inner surface of the needle cover 113, increasing the force needed to move the needle cover 113 proximally with respect to the body 103 of the device 110.

FIGS. 5A to 5D shows features of an embodiment of a medicament delivery device 500, which is also referred to herein as an injector device. These Figures each show a cross section of the one half of the device 500 during various stages of activation of the device.

The device has a distal end 502 and a proximal end 504. The device 500 has a needle 506 for injecting medicament into a user at an injection site, a needle cover 508 and a body 510. The body 510 is configured to be gripped by a user. The body 510 forms part of the external surface of the device. The device 500 houses a pre-filled syringe 512. The needle 506 is in fluid communication with the pre-filled syringe 512 and extends from the distal end of the pre-filled syringe 512. The needle cover 508 is axially movable relative to the body 510 between an initial position, shown in FIG. 5A, in which the needle cover 508 covers the needle 506, and an activated position, shown in FIG. 5D, for dispensing medicament from the device. In the activated position, the needle 506 protrudes from the distal end of the needle cover 508.

The needle cover 508 has one or more first slots and one or more second slots, as described in further detail below.

A spring may exert a spring force against the needle cover 508 which biases the needle cover axially, in the distal direction. A force can be applied by a user against the force of the spring to move the needle cover 508 from the position shown in FIG. 5A towards the position shown in FIG. 5D.

Medicament is dispensed from the medicament delivery device 500 via the needle 506 while the needle cover 508 is in the activated position. An automated mechanism is triggered to start the dispensing of medicament when the needle cover 508 reaches a predetermined axial position within the housing. The predetermined position is located just distally of the activated position.

The automated mechanism may comprise a plunger which is automatically released when the needle cover 508 reaches the predetermined axial position. When the plunger is released it moves within the pre-filled syringe to dispense medicament from the syringe through the needle 506.

Typically the user removes a cap from the distal end of the medicament delivery device 500. The user presses the needle cover 508 against an injection site to move the needle cover 508 axially relative to the body 510 and to uncover the needle 506. The needle 506 is pushed into the injection site. The automated mechanism is released, and medicament is automatically dispensed from the device via the needle 506. The user holds the needle cover 508 in the activated position while the medicament is dispensed.

FIG. 5A shows the device 500 in a pre-use state, which may also be called an initial state or initial position. The needle cover 508 covers the needle 506 in this position. The device 500 also comprises a carrier 514, which supports the pre-filled syringe 512. The carrier 514 comprises a resilient member 516 which takes the form of a flexible arm which extends axially (or longitudinally) and which has a protrusion 518 on the free end of the flexible arm. The protrusion 518 extends radially from the flexible arm to engage with a first slot in the needle cover 508.

Although one resilient member 516 is shown in FIG. 5A, the carrier 514 may comprise two or more resilient members

516. For example, two resilient members 516 may be disposed opposite each other on the carrier 514 and may engage with corresponding slots in the needle cover 508.

FIG. 5B shows the device 500 at the start of an activation movement. A distal force is applied via the body 510 while the needle cover 508 is placed against the user's skin, causing the needle cover 508 to move proximally into the device 500. During this initial movement, the resilient member 516 is deflected and exits the first slot in the needle cover 508. The resilient member 516 abuts an inner surface of the needle cover 508 resulting in a normal force between these components. In particular, the flexible arm of the resilient member 516 bends inwards as the protrusion 518 exits the first slot. The protrusion 518 then remains in contact with an inner surface of the needle cover 508.

FIG. 5C shows the device 500 in a mid-activation state. In this position, the needle cover 508 has moved proximally to an intermediate position and the needle 506 has protruded from the end of the needle cover 508. The medicament dispensing mechanism of the device 500 has not yet been triggered. In this intermediate position, the resilient member 516 is configured to enter a second slot in the needle cover 508. The resilient member 516 is no longer deflected and is again in a relaxed position. Thus the resilient member 516 does not exert any normal or friction force on the needle cover 508 in this position.

FIG. 5D shows the device 500 in an activated state. In this position the needle cover 508 is fully displaced into the device 500 and is in an activated position. The needle 506 protrudes from the end of the needle cover 508 to its maximum extend and the medicament dispensing mechanism of the device 500 is triggered. As can be seen, the resilient member 516 remains in the second slot of the needle cover 508. Thus the resilient member 516 does not exert any normal or friction force on the needle cover 508 in this position.

As the protrusion 518 is in contact with an inner surface of the needle cover 508 during movement of the needle cover 508 between the initial position and the intermediate position, this portion of the movement requires a higher amount of force to achieve than the subsequent movement from the intermediate position to the activated position. The activation force on the needle cover 508 required after the intermediate position is reached is reduced compared to other devices.

After the medicament has been delivered, during removal of the device 500, the sequence of FIGS. 5A to 5D is reversed.

Figure 6A:
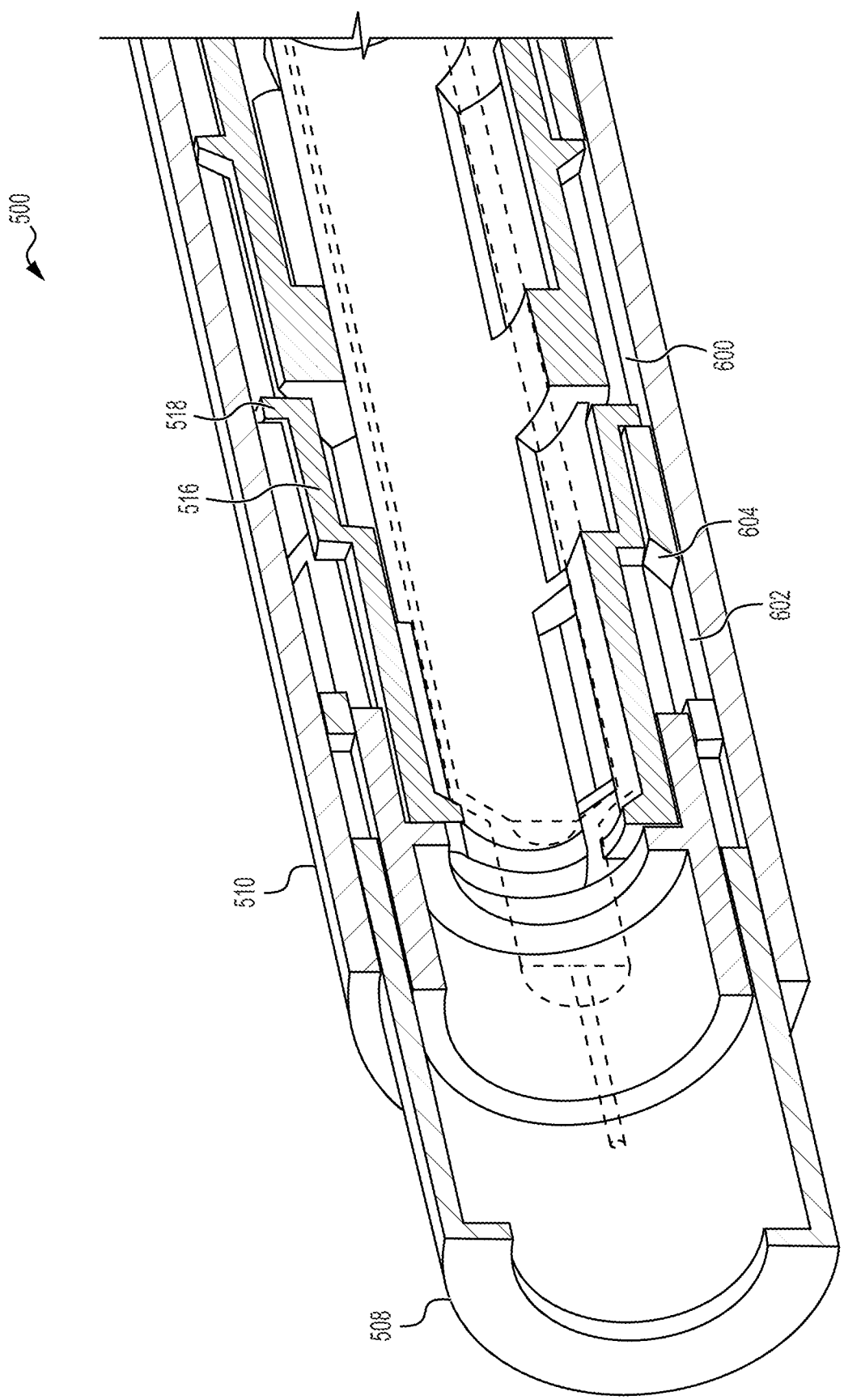
FIG. 6A is a perspective view of a cross section of the medicament delivery device in the initial state of FIG. 5A.

FIG. 6A is a perspective view of a cross section of the device 500 in the initial state (as also shown in FIG. 5A). In this Figure, the needle cover 508 is in the initial position. The protrusion 518 of the resilient member 516 abuts a proximally facing end face of a first slot 600 in the needle cover 508. The first slot 600 extends axially and is an aperture through the wall of the needle cover 508. In some other embodiments, the first slot 600 may be provided as a recess in the inner surface of the needle cover 508, which does not extend completely through the wall of the needle cover 508, but which is deep enough to accommodate the resilient member 516 in a relaxed state.

Figure 6B:
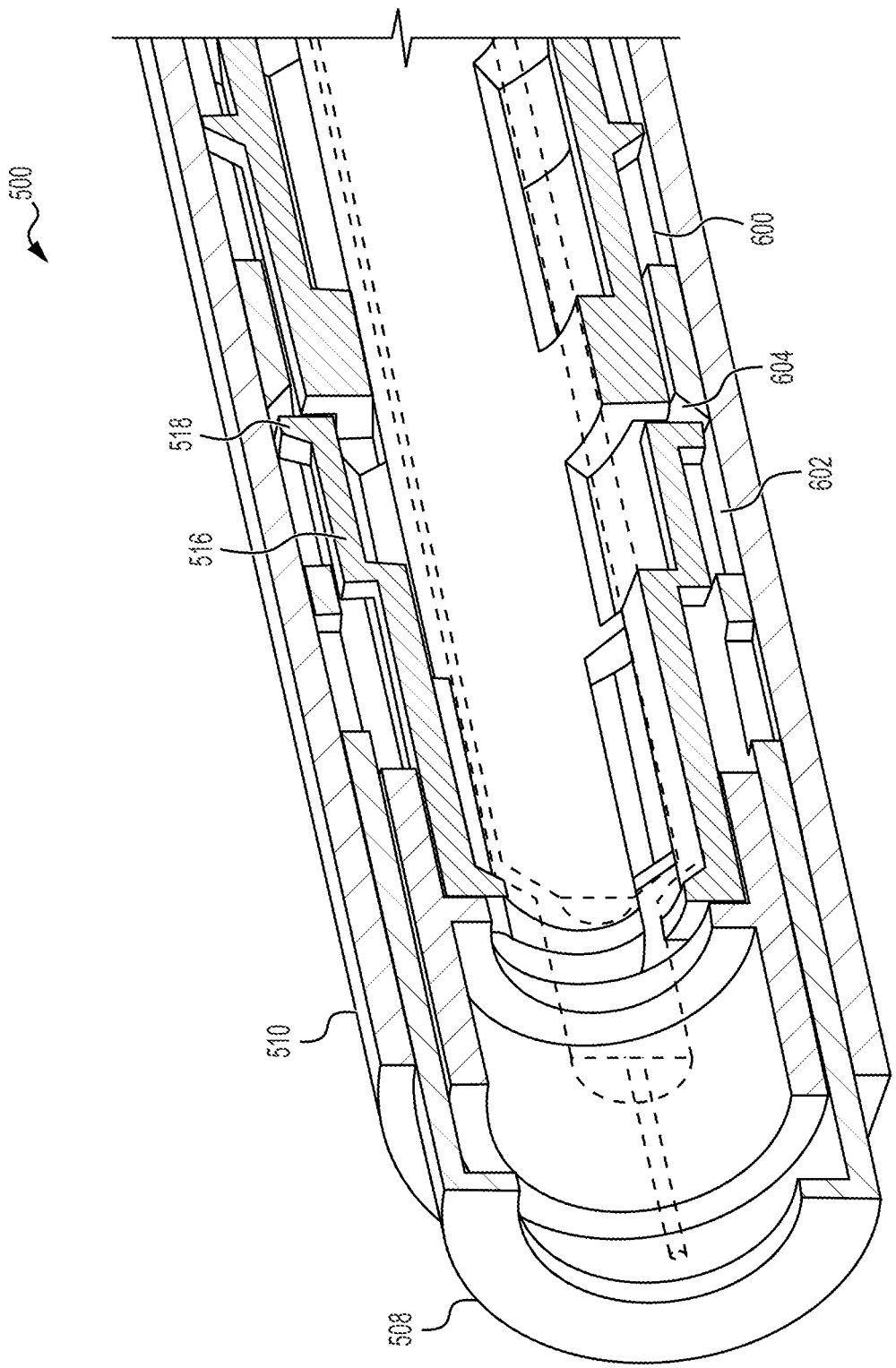
FIG. 6B is a perspective view of a cross section of the medicament delivery device in the intermediate position of FIG. 5C.

FIG. 6B is a perspective view of a cross section of the device 500 in a mid-activation state (as also shown in FIG. 5C). In this position, the needle cover 508 has moved proximally to an intermediate position and the needle 506 has protruded from the end of the needle cover 508. The medicament dispensing mechanism of the device 500 has not yet been triggered.

In this intermediate position, the resilient member 516 is configured to enter a second slot 602 in the needle cover 508. The resilient member 516 is no longer deflected and is again in a relaxed position. The resilient member 516 remains in the second slot 602 until and during the activated position and the second slot 602 may guide the movement of the resilient member 516 between the intermediate and activated positions.

There may be zero normal force between the resilient members 516 and the needle cover 508 when the resilient members are located in the second slots 602. Thus the resilient member 516 does not exert any normal or friction force on the needle cover 508 in this position, or during movement between this position and the activated position (as shown in FIG. 5D). The second slot 602 extends axially and is an aperture through the wall of the needle cover 508. In some other embodiments, the second slot 602 may be provided as a recess in the inner surface of the needle cover 508, which does not extend completely through the wall of the needle cover 508, but which is deep enough to accommodate the resilient member 516 in a relaxed state.

During movement between the initial position of FIG. 6A and intermediate position of FIG. 6B, the flexible arm of the resilient member 516 bends inwards as the protrusion 518 disengages from the first slot 600. The protrusion 518 then remains in contact with an inner surface of the needle cover 508 for a short distance, until the protrusion 518 enters the second slot 602.

In the embodiment depicted, the carrier 514 comprises two resilient members 516 on opposite sides and there are two corresponding first slots 600 and two corresponding second slots 602 in the needle cover 508. In general, a symmetrical arrangement of resilient members 516 may help to ensure a consistent force profile when the device 500 is used.

As can be seen in FIGS. 6A and 6B, the distal facing edge 604 of the second slot 602 is beveled. This can ensure that the change in resistance as the needle cover 508 is moved into the device 500 is gradual and the force profile of the movement is smoothed, as described in more detail with reference to FIG. 7. The distal facing edge of the protrusion 518 of the resilient member 516 may also be beveled, as shown in FIGS. 5A-5D. Again, this can ensure a smoother force profile during initial movement of the needle cover 508.

Figure 7:
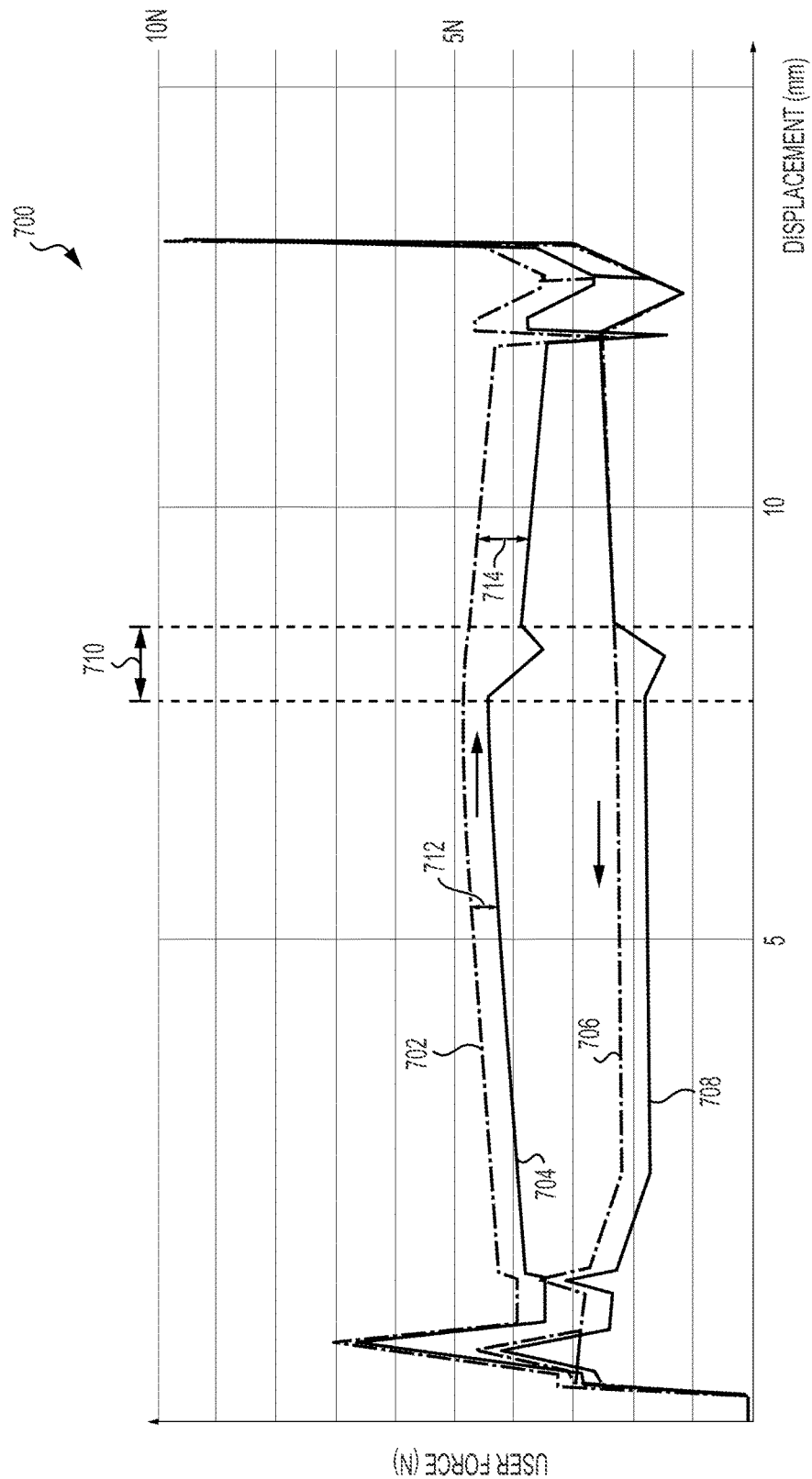
FIG. 7 is a force profile graph illustrating the force profile of a first device and a medicament delivery device.

Referring to FIG. 7, a force profile graph 700 is shown illustrating the force profile of the device 110 and the device 500. The horizontal axis is the displacement of the needle cover is millimeters (mm) and the vertical axis is the user applied force in Newtons (N).

The first trace 702 shows the force profile of the activation force of the device 110 when the user is pushing the device 110 onto their body. The second trace 704 shows the force profile of the activation force of the medicament delivery device 500 when the user is pushing the device 500 onto their body. The third trace 706 shows the force profile of the device 110 when the user is removing the device 110 from their body. The fourth trace 708 shows the force profile of the medicament delivery device 500 when the user is removing the device 500 from their body.

The region 710 between the dashed lines illustrates the displacement region in which the beveled edge 604 of the second slots 602 are located. The second trace 704 shows an overall drop in required user force in this displacement region, coinciding with the point in the movement of the needle cover 508 during which the resilient members 516 transition from a deflected state to a relaxed state as they enter respective second slots 602 in the needle cover 508.

The position of the second slot 602 and angle and length of the beveled edge 604 of the second slot 602 can be adjusted to change the position of the region 710 and/or optimize the force profile within that region 710. For example, it may be advantageous to position the second slot 602 so that the resilient member 516 is in a fully relaxed state before the needle 506 protrudes beyond the end of the needle cover 508. In this case, there will be no extra frictional force from the resilient member 516 as the user is pushing the needle 506 into their skin. This results in a smooth force profile during needle insertion and may help to ensure that the needle is easy to insert to the correct depth for all users, including those with low strength or dexterity. The beveled edge 604 also facilitates the flexing of the resilient member 516 during removal of the device 500 from the user's body.

Alternatively, the second slot 602 may be positioned, and the length of the beveled edge 604 chosen, so that the frictional force produced by the resilient member 516 gradually decreases at the same time as the needle 506 is entering the user's skin. In this case, the extra activation force from the resilient member 516 may decrease at the same time as the resistance from the needle 506 entering the user's skin is increasing, resulting in a more consistent activation force profile. This may result in a smother and less painful needle insertion.

As an alternative or in addition to the beveled edge 604 of the second slot 602, the proximal or outward facing edge of the protrusion 518 may be beveled. This would also achieve the effect of controlling the force profile during insertion and allowing the flexing of the resilient member 516 during removal of the device 500 from the user's body. There may be additional advantages in terms of manufacture of the parts, for example because the needle cover 508 would not need any beveled edges if these are all provided on the carrier 514.

First arrow 712 indicates the difference in activation force between the first device 110 and the medicament delivery device 500 during initial movement of the needle cover away from the pre-use position. The lower activation force (of approx. 0.5 N) is achieved by using a spring of lower force to bias the needle cover. The force of the spring is chosen to overcome the frictional forces on the needle cover and cause it to return to the pre-use position when it is removed from the body. As the friction forces in the medicament delivery device 500 are reduced due to the presence of the second slots 602 and relaxed position of the resilient member 516 in the intermediate and activated positions, a weaker spring can be used.

Second arrow 714 indicates the difference in activation force between the first device 110 and the medicament delivery device 500 during movement between the intermediate position (occurring at approximately the right hand dashed line) and the activated position (maximum displacement of the needle cover). The lower activation force (of approx. 1 N) in this region is due to the reduced or zero friction between the carrier 514 and needle cover 508 and the weaker spring.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F (ab) and F (ab') 2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the devices and methods disclosed herein include, for example, Fab fragments, F (ab') 2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014(E). As described in ISO 11608-1: 2014(E), needle-based injection systems may be broadly distinguished into multi-dose container systems and single-dose (with partial or full evacuation) container systems. The container may be a replaceable container or an integrated non-replaceable container.

As further described in ISO 11608-1: 2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014(E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

The invention claimed is:

1. A medicament delivery device comprising:
    a body;
    a needle for injecting a medicament, the needle disposed at a distal end of the medicament delivery device;
    a needle cover axially movable relative to the body between an extended position, in which a distal end of the needle cover is distal to a distal end of the needle, and a retracted position for dispensing the medicament from the medicament delivery device, wherein when the needle cover is in the retracted position the distal end of the needle is distal to the distal end of the needle cover, the needle cover comprising one or more first slots and one or more second slots; and
    a carrier configured to support a syringe such that when the syringe is disposed in the carrier, an inward protrusion located at a distal end of the carrier engages a neck portion of the syringe, the carrier configured to be disposed within the needle cover and comprising one or more resilient members,
    wherein each resilient member of the one or more resilient members are is configured to (i) engage with a respective slot of the one or more first slots when the needle cover is in the extended position, and (ii) enter a respective slot of the one or more second slots after a proximal movement of the needle cover relative to the body from the extended position to an intermediate position between the extended position and the retracted position.

2. The medicament delivery device of claim 1, wherein the medicament delivery device is configured such that when the needle cover is between the extended position and the intermediate position, each resilient member of the one or more resilient members is configured to be deflected to contact an inner surface of the needle cover.

3. The medicament delivery device of claim 1, wherein the medicament delivery device is configured such that the proximal movement of the needle cover proximally from the extended position causes the one or more resilient members to disengage from the one or more first slots.

4. The medicament delivery device of claim 1, wherein each resilient member of the one or more resilient members is configured to remain in the one or more second slots during the proximal movement of the needle cover relative to the body between the intermediate position and the retracted position.

5. The medicament delivery device of claim 1, wherein there is a zero normal force between the one or more resilient members and the needle cover when the one or more resilient members are in the one or more second slots.

6. The medicament delivery device of claim 1, wherein each resilient member of the one or more resilient members comprises a flexible arm and a protrusion disposed on an end of the flexible arm.

7. The medicament delivery device of claim 6, wherein the protrusion is configured to:
    engage with the respective slot of the one or more first slots when the needle cover is in the extended position;
    enter the respective slot of the one or more second slots after the proximal movement of the needle cover from the extended position to the intermediate position; and
    contact an inner surface of the needle cover between the extended position and the intermediate position.

8. The medicament delivery device of claim 6, wherein a distal facing edge of the protrusion is beveled.

9. The medicament delivery device of claim 6, wherein a proximal or outward facing edge of the protrusion is beveled.

10. The medicament delivery device of claim 1, wherein the one or more first slots or the one or more second slots are apertures extending through the needle cover.

11. The medicament delivery device of claim 1, wherein the one or more first slots or the one or more second slots are recesses defined by an inner surface of the needle cover.

12. The medicament delivery device of claim 1, further comprising a spring configured to exert a force which biases the needle cover axially towards the distal end of the medicament delivery device.

13. The medicament delivery device of claim 1, wherein a distal facing edge of each slot of the one or more second slots is beveled.

14. The medicament delivery device of claim 1, wherein the needle is configured to begin protruding from the distal end of the needle cover during movement of the needle cover between the intermediate position and the retracted position.

15. The medicament delivery device of claim 1, further comprising the syringe containing the medicament.

16. A medicament delivery device comprising:
a body;
a needle for injecting a medicament, the needle disposed at a distal end of the medicament delivery device;
a needle cover configured to be moved in a proximal direction into the body of the medicament delivery device to expose a distal end of the needle from a distal end of the needle cover;
a carrier disposed within the needle cover such that when a syringe is disposed in the carrier, an inward protrusion located at a distal end of the carrier engages a neck portion of the syringe, the carrier comprising one or more flexible arms, each of the one or more flexible arms configured such that
prior to a movement of the needle cover relative to the body of the medicament delivery device, the one or more flexible arms are retained in a respective first slot, aperture, or recess in the needle cover;
during an initial portion of the movement of the needle cover relative to the body, the one or more flexible arms are forced out of the respective first slot, aperture, or recess in the needle cover; and
during a subsequent portion of the movement of the needle cover relative to the body, the one or more flexible arms move out of engagement with the needle cover to reduce a force required to move the needle cover in the proximal direction into the body of the medicament delivery device.

17. The medicament delivery device of claim 16, wherein the needle cover is configured to be moved in the proximal direction into the body of the medicament delivery device when a force is applied in the proximal direction to a distal end surface of the needle cover.

18. The medicament delivery device of claim 16, wherein during the initial portion of the movement of the needle cover relative to the body, each flexible arm of the one or more flexible arms are configured to be deflected by contact with a surface of the needle cover.

19. The medicament delivery device of claim 16, wherein during the initial portion of the movement of the needle cover relative to the body, each flexible arm of the one or more flexible arms are biased against a surface of the needle cover.

20. The medicament delivery device of claim 19, wherein during the initial portion of the movement of the needle cover relative to the body, the one or more flexible arms exert a force against the surface of the needle cover which increases the force required to move the needle cover in the proximal direction into the body of the medicament delivery device.

21. The medicament delivery device of claim 19, wherein the surface of the needle cover comprises an inner circumferential surface.

22. The medicament delivery device of claim 16, wherein during the subsequent portion of the movement of the needle cover relative to the body, each flexible arm of the one or more flexible arms are configured to move out of the engagement with the needle cover by entering a respective second slot, aperture, or recess in the needle cover.

23. The medicament delivery device of claim 22, wherein the one or more flexible arms exert a zero normal force against the needle cover when the one or more flexible arms are out of the engagement with the needle cover.

24. The medicament delivery device of claim 22, wherein the one or more flexible arms exert a zero frictional force against a proximal movement of the needle cover when the one or more flexible arms are out of the engagement with the needle cover.

25. The medicament delivery device of claim 22, wherein each flexible arm of the one or more flexible arms are configured to remain out of the engagement with the needle cover for a remainder of the movement of the needle cover relative to the body.

26. The medicament delivery device of claim 22, wherein a distal facing edge of the respective second slot, aperture, or recess is beveled.

27. The medicament delivery device of claim 16, wherein each flexible arm of the one or more flexible arms comprises a protrusion disposed on a free end of each flexible arm.

28. The medicament delivery device of claim 27, wherein the protrusion is configured to:
prior to the movement of the needle cover relative to the body, be retained in the respective first slot, aperture, or recess in the needle cover when the needle cover is in an extended position;
contact an inner surface of the needle cover during a proximal movement of the needle cover between the extended position and an intermediate position; and
enter a respective second slot, aperture, or recess in the needle cover when the needle cover reaches the intermediate position.

29. The medicament delivery device of claim 27, wherein a distal facing edge of the protrusion is beveled or a proximal or outward facing edge of the protrusion is beveled.

30. The medicament delivery device of claim 16, further comprising a spring configured to exert a force which biases the needle cover axially towards the distal end of the medicament delivery device.

* * * * *

UNITED STATES PATENT AND TRADEMARK OFFICE
CERTIFICATE OF CORRECTION

| | | |
|---|---|---|
| PATENT NO. | : 12,268,858 B1 | Page 1 of 1 |
| APPLICATION NO. | : 18/594683 | |
| DATED | : April 8, 2025 | |
| INVENTOR(S) | : Alexander Hee-Hanson et al. | |

It is certified that error appears in the above-identified patent and that said Letters Patent is hereby corrected as shown below:

In the Claims

Column 16, Line 15 (approx.), Claim 1, after "members" delete "are"

Signed and Sealed this
Tenth Day of June, 2025

Coke Morgan Stewart
*Acting Director of the United States Patent and Trademark Office*